United States Patent
Portal

(10) Patent No.: US 8,283,378 B2
(45) Date of Patent: Oct. 9, 2012

(54) PHENYLUREA INHIBITORS OF THE SOAT-1 ENZYME AND PHARMACEUTICAL/COSMETIC COMPOSITIONS COMPRISED THEREOF

(75) Inventor: Thibaud Portal, Opio (FR)

(73) Assignee: Galderma Research & Development, Biot (FR)

( * ) Notice: Subject to any disclaimer, the term of this patent is extended or adjusted under 35 U.S.C. 154(b) by 150 days.

(21) Appl. No.: 12/718,073

(22) Filed: Mar. 5, 2010

(65) Prior Publication Data

US 2010/0222431 A1    Sep. 2, 2010

Related U.S. Application Data

(63) Continuation of application No. PCT/EP2008/061779, filed on Sep. 5, 2008.

(60) Provisional application No. 60/960,095, filed on Sep. 14, 2007.

(30) Foreign Application Priority Data

Sep. 6, 2007  (FR) .................................... 07 57395

(51) Int. Cl.
    *A01N 55/06*    (2006.01)
    *A61K 31/305*    (2006.01)
(52) U.S. Cl. .......................................... 514/596; 564/48
(58) Field of Classification Search .................. 514/596; 564/48
    See application file for complete search history.

(56) References Cited

U.S. PATENT DOCUMENTS 5,106,873 A    4/1992  O'Brien et al.
6,133,326 A *  10/2000 Mayne .......................... 514/346

OTHER PUBLICATIONS

Medicine on Line—Hypercholesteroemia (2004), 2 pages.*
Mayo Clinic Staff (2012), 15 pages.*
Medicine on Line (Feb. 3, 2011), 3 pages.*
Trivedi et al., "Inhibitors of Acyl-CoA:Cholesterol Acyltransferase. 4. A Novel Series of Urea ACAT Inhibitors as Potentially Hypocholesterolemic Agents" J. Med. Chem., 1993, pp. 3300-3307, vol. 36, American Chemical Society, WDC.
O'Brien et al., "Inhibitors of Acyl-CoA:Cholesterol O-Acyl Transferase (ACAT) as Hypocholesterolemic Agents. 8. Incorporation of Amide or Amine Functionalities into a Series of Disubstituted Ureas and Carbamates. Effects on ACAT Inhibition in Vitro and Efficacy in Vivo." J. Med. Chem., 1994, pp. 1810-1822, vol. 37, American Chemical Society, WDC.
Bellemin et al., "New indole derivatives as ACAT inhibitors: synthesis and structure-activity relationships", Eur. J. Med. Chem., 1996, pp. 123-132, vol. 31, Editions Scientifique Elsevier, Paris, France.

* cited by examiner

*Primary Examiner* — Brandon Fetterolf
*Assistant Examiner* — Shirley V Gembeh
(74) *Attorney, Agent, or Firm* — SNR Denton US LLP

(57) ABSTRACT

Novel phenylurea compounds of formula (I):

and cosmetic and pharmaceutical compositions containing same are useful for treating disorders of the sebaceous gland, e.g., acne, or have cosmetic applications.

22 Claims, No Drawings

PHENYLUREA INHIBITORS OF THE SOAT-1 ENZYME AND PHARMACEUTICAL/COSMETIC COMPOSITIONS COMPRISED THEREOF

CROSS-REFERENCE TO EARLIER APPLICATIONS

This application is a continuation of PCT/EP 2008/061779, filed Sep. 5, 2008 and designating the United States (published in the English language on Mar. 12, 2009 as WO 2009/030752 A1), which claims benefit under 35 U.S.C. §119 (e) of U.S. Provisional Application No. 60/960,095, filed Sep. 14, 2007 and claims foreign priority under 35 U.S.C. §119 of Application No. 0757395, filed Sep. 6, 2007 in France, each hereby expressly incorporated by reference in its entirety and each assigned to the assignee hereof.

BACKGROUND OF THE INVENTION

1. Technical Field of the Invention

The present invention relates to novel phenylurea compound inhibitors of the SOAT-1 enzyme (abbreviation of "Sterol-O-Acyl Transferase-1", also called ACAT-1 from "Acylcoenzyme A Cholesterol Acyl Transferase"). It also relates to their formulation into pharmaceutical compositions useful for application in human or veterinary medicine, or in cosmetic compositions, as well as their non-therapeutic applications.

2. Description of Background and/or Related and/or Prior Art

Compounds having a SOAT-1 inhibiting type of activity are widely described in the literature, as having activities in the regulation of the biological processes involving cholesterol and its derivatives. These properties endow compounds of this class with considerable potential in the treatment or prevention of a great many pathologies, and more particularly in dermatology and in cardiovascular diseases or disorders of the central nervous system. Most of the biological effects of the inhibitors of SOAT-1 are mediated by prevention of the synthesis of cholesterol esters by the SOAT-1 enzyme. Among the documents of the prior art describing SOAT-1 inhibiting molecules, exemplary are WO 96/10559, EP-0370740, EP-0424194, U.S. Pat. No. 4,623,663, EP-0557171, U.S. Pat. No. 5,003,106, EP-0293880, EP-0433662, U.S. Pat. No. 5,106,873 which describe compounds for treating arteriosclerosis or hypercholesterolaemia. The therapeutic potential of the inhibitors of SOAT-1 in the treatment of cardiovascular diseases and in particular of hypercholesterolaemia and arteriosclerosis is also described in Kharbanda R. K. et al., in *Circulation*. 2005, 11, 804. The potential of the inhibitors of SOAT-1 for the treatment of Alzheimer's disease has also been reported in the literature, for example by Puglielli, L. et al., in *Nature Neurosciences* 2003, 6 (4), 345.

For their part, U.S. Pat. Nos. 6,133,326, 6,271,268, and WO 2005/034931 describe SOAT-1 inhibiting compounds for inhibiting the production of sebum. In the field of dermatology in particular, it is particularly advantageous to prevent excessive production of sebum and all the associated conditions.

Sebum is produced by the sebaceous glands. The highest concentration of sebaceous glands occurs on the face, the shoulders, the back and the scalp. Sebum is secreted on the surface of the skin, where it plays a very important physiological role, associated with maintenance of the dermal barrier and of a microenvironment permitting regulation of the bacterial and fungal flora of the skin.

Hyperproduction of sebum is generally associated with a skin or scalp of greasy appearance, causing discomfort and a poor appearance. Moreover, hyperproduction of sebum can give rise to seborrhoeic dermatitis and is associated with an increased incidence or severity of acne. The cholesterol esters produced in the sebaceous gland by SOAT-1 are one of the components of sebum, among several classes of lipids including triglycerides, esters of waxes and squalenes, as described by Nikkari, T., in *J Invest Derm* 1974, 62, 257. Inhibition of this enzyme or of other acyltransferases may therefore make it possible to inhibit the production of sebum. U.S. Pat. No. 6,133,326 describes, notably, the inhibition of sebum by inhibitors of ACAT-1 (also called SOAT-1). However, to date, no treatment utilizing said inhibitors is commercially available. The only treatments providing cure or relief of disorders associated with hyperseborrhoea are systemic hormonal treatments or systemic treatment with 13-cis retinoic acid, and the side effects of these treatments limit their field of application considerably. There is therefore a clear medical and cosmetic need for treatment of the disorders and pathologies associated with hyperproduction of sebum.

SUMMARY OF THE INVENTION

The present invention features novel phenylurea compounds which display inhibitory action on the SOAT-1 enzyme.

Thus, this invention features novel phenylurea compound inhibitors of the SOAT-1 enzyme, having the following general formula (I):

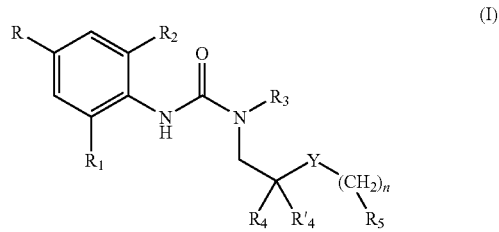

in which,
Y is O or $S(O)_p$,
p is equal to 0 or 2,
n is equal to 0, 1 or 2,
R is a hydrogen atom, a $(C_1-C_6)$alkyl radical, a —$CH_2$—$NR_6R_7$ radical, a —$C(O)$—$NR_6R_7$ radical or a —$C(S)$—$NR_6R_7$ radical, wherein $R_6$ is a hydrogen atom or a $(C_1-C_4)$ alkyl radical and $R_7$ is a hydrogen atom, a phenyl or a cycloalkyl radical,
$R_1$ is a hydrogen atom, a $(C_1-C_6)$alkyl radical or an atom of chlorine, bromine or fluorine,
$R_2$ is a $(C_1-C_6)$alkyl radical,
$R_3$ is a hydrogen atom or a $(C_1-C_6)$alkyl radical,
$R_4$ and $R'_4$ are identical and are each a $(C_1-C_6)$alkyl radical or alternatively $R_4$ and $R'_4$ are joined together and form, with the carbon atom from which they depend, a cycloalkyl group, an indanyl group, or a saturated heterocyclic group selected from the groups piperidine, tetrahydropyran, pyrrolidine, tetrahydrothiophene, tetrahydrofuran and azetidine, wherein the groups piperidine, pyrrolidine and azetidine are optionally substituted on the nitrogen atom, with an $R_8$, —$C(O)R_8$ or —$SO_2R_8$ radical, wherein $R_5$ is a $(C_1-C_4)$alkyl radical, $R_5$ is an unsubstituted phenyl radical or a phenyl radical substituted with one to three substituents, which may be identical or different, selected from the atoms of chlorine, bromine or fluorine, the radicals $(C_1$-$C_6)$alkyl, cycloalkyl, trifluoromethyl, hydroxy, phenyl, 2-pyridyl, 3-pyridyl, 4-pyridyl, $(C_1$-$C_6)$alkoxy, phenoxy, $(C_1$-$C_6)$alkylthio, trifluoromethoxy, or —$NR_9R_{10}$, wherein $R_9$ and $R_{10}$, which may be identical or different, represent, each independently, a hydrogen atom or a $(C_1$-$C_4)$alkyl radical, as well as their pharmaceutically acceptable salts, solvates or hydrates.

"Alkyl radical" means a saturated, linear or branched hydrocarbon chain. $(C_1$-$C_6)$alkyl means an alkyl chain having from 1 to 6 carbon atoms. Exemplary of $(C_1$-$C_6)$alkyl are methyl, ethyl, n-propyl, isopropyl, n-butyl, tert-butyl, sec-butyl, pentyl, and hexyl radicals. "$(C_1$-$C_4)$alkyl" means an alkyl chain having from 1 to 4 carbon atoms. Exemplary of $(C_1$-$C_4)$alkyl are methyl, ethyl, n-propyl, isopropyl, n-butyl, tert-butyl, and sec-butyl radicals.

$(C_1$-$C_6)$alkoxy is an —O—$(C_1$-$C_6)$alkyl radical.

$(C_1$-$C_6)$alkylthio is an —S—$(C_1$-$C_6)$alkyl radical.

Phenoxy is an —O-phenyl radical.

"Cycloalkyl radical" is a saturated, cyclic hydrocarbon chain, having from 3 to 7 carbon atoms. Exemplary of cycloalkyl radicals are the cyclopropyl, cyclobutyl, cyclopentyl, cyclohexyl and cycloheptyl radicals.

DETAILED DESCRIPTION OF BEST MODE AND SPECIFIC/PREFERRED EMBODIMENTS OF THE INVENTION

The compounds of formula (I) defined above are preferred, in which:

Y is O, $S(O)_p$, p is equal to 0 or 2, n is equal to 0, 1 or 2,

R is a hydrogen atom, $R_1$ is a methyl, ethyl, isopropyl or tert-butyl radical, $R_2$ is a methyl, ethyl, isopropyl or tent-butyl radical, $R_3$ is a hydrogen atom, $R_4$ and $R'_4$ are identical and are each an ethyl radical or alternatively $R_4$ and $R'_4$ are joined together and form, with the carbon atom from which they depend, either a cyclopentyl, cyclohexyl, cycloheptyl, or indanyl group, or a tetrahydropyran group, piperidine group, or piperidine group substituted on the nitrogen atom with an $R_8$, —C(O)$R_8$ or —SO$_2R_8$ radical, wherein $R_8$ is a $(C_1$-$C_4)$alkyl radical, $R_5$ is an o-, m-, or p-biphenyl, o-, m- or p-iodophenyl, o-, m-, or p-(2-pyridyl)phenyl, o-, m-, or p-(3-pyridyl)phenyl or o-, m-, or p-(4-pyridyl)phenyl radical, an unsubstituted phenyl radical, a phenyl radical substituted with one to three substituents, identical or different, selected from methyl, ethyl, trifluoromethyl, fluorine, chlorine, hydroxy, as well as their pharmaceutically acceptable salts, solvates or hydrates.

According to the present invention, among the compounds of formula (I) as defined above, those are more particularly preferred that have one or a combination of the following characteristics, when they are not mutually exclusive:

n is equal to 0 or 1,

R is a hydrogen atom, $R_1$ is an isopropyl radical, $R_2$ is an isopropyl radical, $R_3$ is a hydrogen atom, $R_4$ and $R'_4$ are joined together and form, with the carbon atom from which they depend, a cyclopentyl, cyclohexyl or indanyl group, $R_5$ is an unsubstituted phenyl radical or a phenyl radical substituted with a methyl radical, for example in the para position, or with a phenyl radical, for example in the ortho position.

The compounds of formula (I) given below, as well as their pharmaceutically acceptable salts, solvates or hydrates, are particularly preferred:

1-(1-Benzenesulfonyl-cyclopentylmethyl)-3-(2,6-diisopropyl-phenyl)-urea, compound (I.1) with Y=—S(O)$_p$, p=2, n=0, R=H, $R_1$=$R_2$=iPr; $R_3$=H; $R_4$ and $R'_4$ are joined together to form a cyclopentyl; $R_5$=Ph

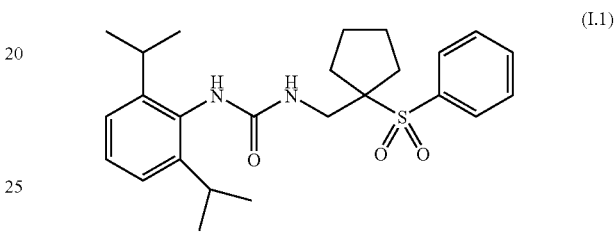

(I.1)

1-(2,6-Diisopropyl-phenyl)-3-[1-(toluene-4-sulfonyl)-cyclopentylmethyl]-urea, compound (I.2) with Y=—S(O)$_p$, p=2, n=0, R=H, $R_1$=$R_2$=iPr; $R_3$=H; $R_4$ and $R'_4$ are joined together to form a cyclopentyl; $R_5$=p-tolyl

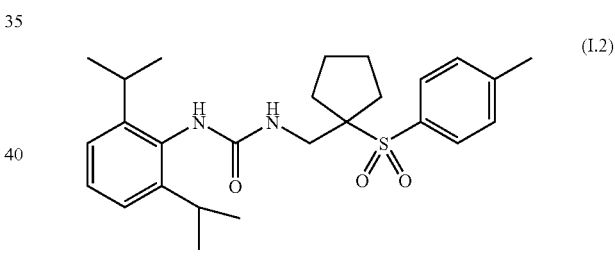

(I.2)

1-(2-Benzenesulfonyl-indan-2-ylmethyl)-3-(2,6-diisopropyl-phenyl)-urea, compound (I.3) with Y=—S(O)$_p$, p=2, n=0, R=H, $R_1$=$R_2$=iPr; $R_3$=H; $R_4$ and $R'_4$ are joined together to form an indanyl; $R_5$=Ph

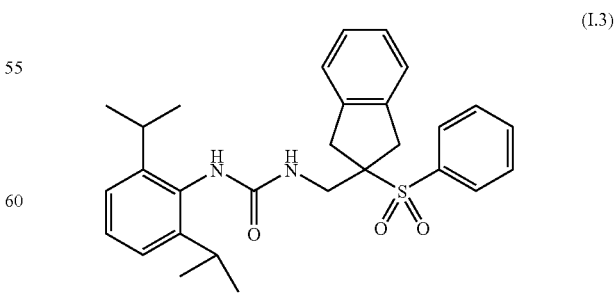

(I.3)

1-(1-Benzylsulfanyl-cyclohexylmethyl)-3-(2,6-diisopropyl-phenyl)-urea, compound (I.4) with Y=S, p=0, n=1, R=H, R₁=R₂=iPr; R₃=H; R₄ and R'₄ are joined together to form a cyclohexyl; R₅=Ph

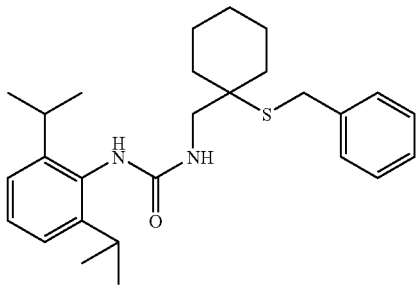

(I.4)

1-(1-Benzyloxy-cyclohexylmethyl)-3-(2,6-diisopropyl-phenyl)-urea, compound (I.5) with Y=O, p=0, n=1, R=H, R₁=R₂=iPr; R₃=H; R₄ and R'₄ are joined together to form a cyclohexyl; R₅=Ph

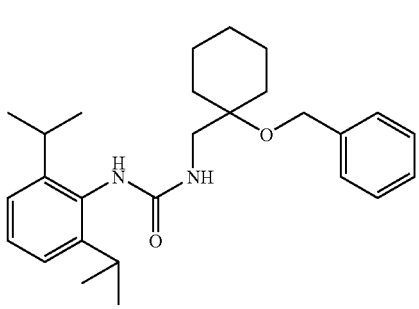

(I.5)

1-(2,6-Diisopropyl-phenyl)-3-(1-phenoxy-cyclohexylmethyl)-urea, compound (I.6) with Y=O, p=0, n=0, R=H, R₁=R₂=iPr; R₃=H; R₄ and R'₄ are joined together to form a cyclohexyl; R₅=Ph

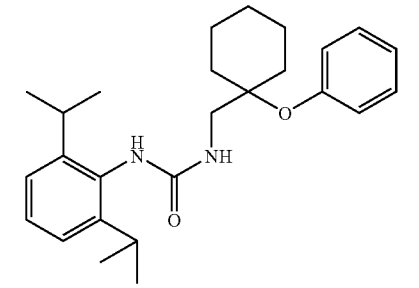

(I.6)

1-(2,6-Diisopropyl-phenyl)-3-(1-phenylsulfanyl-cyclohexylmethyl)-urea, compound (I.7) with Y=S, p=0, n=0, R=H, R₁=R₂=iPr; R₃=H; R₄ and R'₄ are joined together to form a cyclohexyl; R₅=Ph

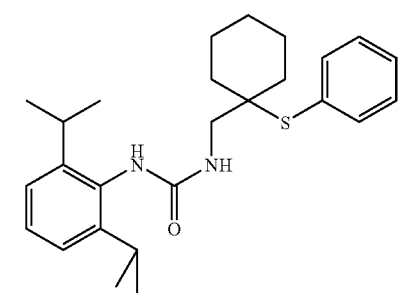

(I.7)

1-(2,6-Diisopropyl-phenyl)-3-(1-p-tolylsulfanyl-cyclohexylmethyl)-urea, compound (I.8) with Y=S, p=0, n=0, R=H, R₁=R₂=iPr; R₃=H; R₄ and R'₄ are joined together to form a cyclohexyl; R₅=p-tolyl

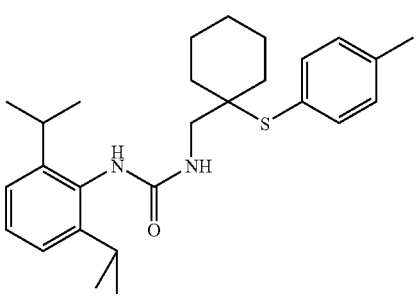

(I.8)

1-[1-(Biphenyl-2-ylsulfanyl)-cyclohexylmethyl]-3-(2,6-diisopropyl-phenyl)-urea, compound (I.9) with Y=S, p=0, n=0, R=H, R₁=R₂=iPr; R₃=H; R₄ and R'₄ are joined together to form a cyclohexyl; R₅=o-BiPh

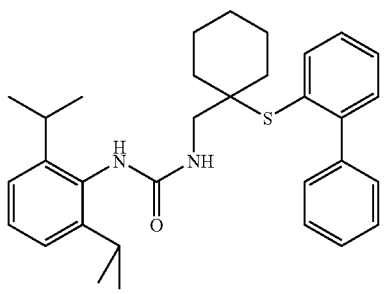

(I.9)

1-[1-(Biphenyl-2-ylsulfanyl)-cyclopentylmethyl]-3-(2,6-diisopropyl-phenyl)-urea, compound (I.10) with Y=S, p=0, n=0, R=H, R₁=R₂=iPr; R₃=H; R₄ and R'₄ are joined together to form a cyclopentyl; R₅=o-BiPh

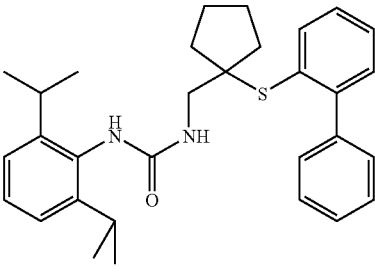

(I.10)

1-[1-(Biphenyl-2-yloxy)-cyclohexylmethyl]-3-(2,6-diisopropyl-phenyl)-urea, compound (I.11) with Y=O, n=0, R=H, R₁=R₂=iPr; R₃=H; R₄ and R'₄ are joined together to form a cyclohexyl; R₅=o-BiPh

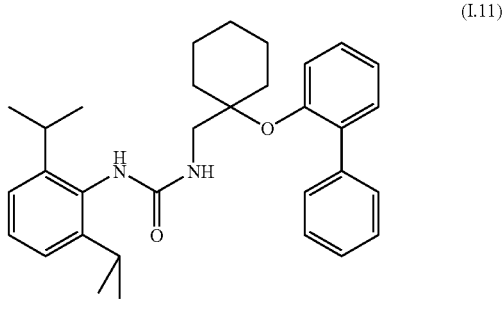

(I.11)

The salts of the compounds according to the invention are prepared according to methods that are well known by one skilled in the art. The salts of the compounds of formula (I) according to the present invention include those with organic or mineral acids that permit convenient separation or crystallization of the compounds of formula (I), as well as pharmaceutically acceptable salts. We may mention, as a suitable acid: picric acid, oxalic acid or an optically active acid, for example a tartaric acid, a dibenzoyltartaric acid, a mandelic acid or a camphosulfonic acid, and those which form physiologically acceptable salts, such as the hydrochloride, hydrobromide, sulfate, hydrogen-sulfate, dihydrogen-phosphate, maleate, fumarate, 2-naphthalenesulfonate, paratoluenesulfonate, the hydrochloride being preferred.

The solvates or hydrates can be obtained directly from the synthesis process, compound (I) being isolated in the form of a hydrate, for example a mono- or hemi-hydrate or of a solvate of the solvent of reaction or purification.

The compounds of formula (I) can be purified by any conventional method of purification, for example by crystallization or purification by column chromatography.

When a compound of formula (I) according to the invention has one or more asymmetric carbons, the optical isomers of this compound form an integral part of the present invention. The compounds of formula (I) can therefore be in the form of a pure isomer or a mixture of isomers in all proportions.

The compounds of formula (I) according to the invention can be prepared according to SCHEME 1 given below, in which R, R₁, R₂, R₃, R₄, R'₄, Y and n are as defined for the compounds of formula (I) and R'₅ is the group R₅ or a group that is a precursor of R₅:

SCHEME 1

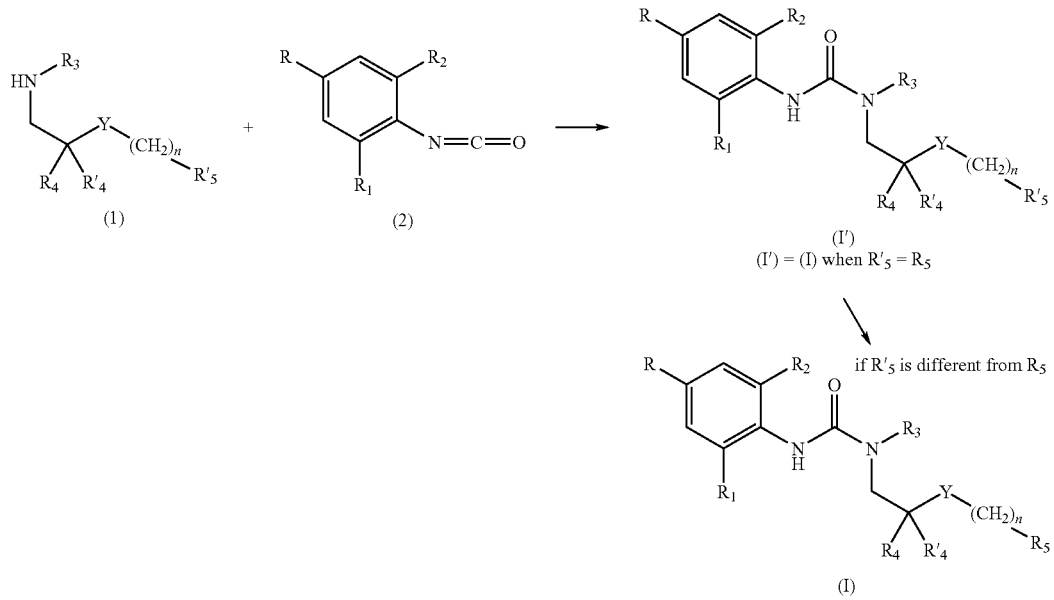

The compounds of general formula (I) can be prepared by addition of the primary or secondary amines of general formula (1) to the corresponding urea precursors, for example the isocyanates (2), for example in accordance with the reactions described by O'Brien, P. M. et al. in *J Med Chem* 1994, 37 (12), 1810-1822. The compounds of formula (1) can bear the R₅=R'₅ group of the desired final compounds of formula (I) directly and in this case the compound (I') corresponds to the desired compound (I), which is the case for example when R₅=o, m, or p-iodo-phenyl. In some cases, the addition can be performed with a compound of formula (1) bearing a group R'₅ that is a precursor of group R₅, to form an intermediate (I') which must then be converted to obtain the desired group R₅. For example, in the preparation of compounds of formula (I) in which R₅=o, m, or p-biphenyl or indeed any isomers of phenyl-pyridine, the compound of formula (I) used comprises a group R'₅=o, m, or p-iodo-phenyl, the iodine being in the position corresponding to the desired phenyl or pyridyl group. The compound of formula (I') which corresponds to the compound of formula (I) in which R'₅=o, m, or p-iodo-phenyl is formed as an intermediate is then submitted to a Suzuki type of coupling reaction or similar, with a corresponding phenylboronic acid or pyridylboronic acid partner, according to the conventional conditions described for example in Suzuki et al., *Synth. Commun.* 1981, 11, 513 or Sharp, M. J. *Tet. Lett.* 1985, 26, 5997) or optimized conditions if necessary (see for example Littke, A. F. et al., *J Am Chem Soc* 2000, 122 (17), 4020-4028).

The primary amines of general formula (1) in which $R_3$=H can be prepared according to SCHEME 2 given below, in which $R_4$, $R'_4$, Y and n are as defined for the compounds of formula (I) and $R'_5$ is the group $R_5$ or a group that is a precursor of $R_5$:

G. M., publ. John Wiley and Sons, 1991 and in "Protecting Groups>>, Kocienski P. J., 1994, Georg Thieme Verlag.

The compounds (I) according to the invention, as well as their pharmaceutically acceptable salts, solvates and/or hydrates, display SOAT-1 enzyme inhibiting properties. This inhibitory effect on the SOAT-1 enzyme is measured by a primary HepG2 enzyme test, as described below. The preferred compounds according to the present invention have a concentration permitting 50% inhibition of the enzyme response ($IC_{50}$) less than or equal to 1200 nM, preferably less than or equal to 500 nM, and advantageously less than or equal to 100 nM.

SCHEME 2

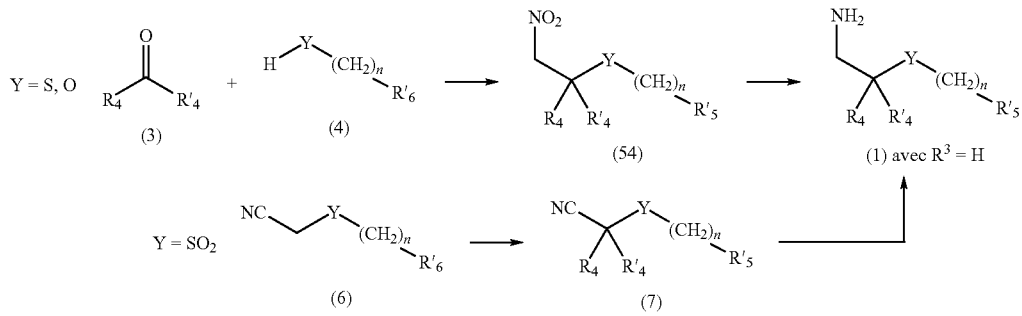

In the case when Y=O or S, the ketones of formula (3) are reacted with nitromethane in a basic medium and then the nucleophile thiol (Y=S) or alcohol (Y=O) of formula (4) is added by a reaction of the Mickaël type to give the nitrated compounds of formula (5), as described for example in Lin, W.-W. et al. *J Org Chem* 2001, 66 (6), 1984-1991 and Schneider, R. et al. *J Heterocycl Chem* 1994, 31 (4), 797-803. The nitro function of the compounds of formula (5) can then be reduced to give the primary amine (1), for example by reaction with $LiAlH_4$, as described in Hegedus, L S.; Perry, R. J.; *J Org Chem* 1984, 49 (14), 2570.

In the case when Y=$SO_2$, the nitriles of formula (7) can be obtained by deprotonation of the acidic methylene of the compounds of formula (6), then substitution with an electrophile $R_4$—X(=$R'_4$—X) where X is a leaving group such as a chlorine (with two equivalents, or one equivalent in the case when $R_4$ and $R'_4$ are joined together to form a ring), for example in accordance with the conditions described in Sakamoto, T. et al., *Heterocycles* 1988, 27, 1353. Once again, reduction of the nitrile function of the compound of formula (7), for example by reaction with a hydride as described above, permits the primary amines of formula (1) to be obtained.

The isocyanates of formula (2) are commercial compounds or can be prepared by techniques that are well known to one skilled in the art.

The functional groups that are optionally present in the reaction intermediates used in the method can be protected, either permanently or temporarily, by protecting groups that ensure definite synthesis of the expected compounds. The reactions of protection and deprotection are performed according to techniques that are well known by one skilled in the art. Temporary protecting group of amines, alcohols or of carboxylic acids means protecting groups such as those described in "Protective Groups in Organic Chemistry", ed. McOmie J. W. F., Plenum Press, 1973, in "Protective Groups in Organic Synthesis", $2^{nd}$ edition, Greene T. W. and Wuts P.

The present invention also features the compounds of formula (I) as described above, as well as their pharmaceutically acceptable salts, pharmaceutically acceptable solvates and/or hydrates, formulated into medicinal compositions.

The present invention also features formulating at least one compound of formula (I), as well as its salts, pharmaceutically acceptable solvates and/or hydrates, into medicinal compositions for preventing and/or treating disorders of the sebaceous gland such as hyperseborrhoea, acne, seborrhoeic dermatitis, atopic dermatitis or rosacea, ocular pathologies such as ocular rosacea, disorders of the meibomian gland, such as blepharitis, meibomitis, chalazion, dry eye, conjunctivitis or keratoconjunctivitis or else pathologies such as hypercholesterolaemia, arteriosclerosis or Alzheimer's disease. The compounds according to the invention are particularly suitable for formulation into pharmaceutical compositions useful for the treatment of acne. The compounds according to the invention are thus also suitable for use in the pathologies listed above.

The present invention also features pharmaceutical or cosmetic compositions comprising, formulated into a physiologically acceptable medium, at least one compound of formula (I) as defined above, or one of its salts, pharmaceutically acceptable solvates and/or hydrates. The compositions according to the invention therefore comprise a physiologically acceptable carrier or at least one physiologically or pharmaceutically acceptable excipient, selected according to the desired cosmetic or pharmaceutical form and the selected mode of administration, whether regime or regimen.

Physiologically acceptable carrier or medium means a carrier that is compatible with the skin, the mucosae and/or the integumentary appendages.

The compositions according to the invention can be administered by the enteral, parenteral, rectal, topical or ocular route, whether regime or regimen. Preferably, the pharmaceutical composition is in a form suitable for topical application.

For administration by the enteral route, the composition, more particularly the pharmaceutical composition, can be in the form of tablets, capsules, coated tablets, syrups, suspensions, solutions, powders, granules, emulsions, microspheres or nanospheres or lipid or polymeric vesicles permitting controlled release. For parenteral administration, the composition can be in the form of solutions or suspensions for infusion or for injection.

The compositions according to the invention contain a compound according to the invention, in sufficient quantity to elicit the desired cosmetic, prophylactic or therapeutic effect. The compounds according to the invention are generally administered at a daily dose ranging from about 0.001 mg/kg to 100 mg/kg of body weight, in 1 to 3 doses. The compounds are administered systemically at a concentration generally ranging from 0.001 to 10 wt. %, preferably from 0.01 to 2 wt. %, relative to the weight of the composition.

For topical administration, the pharmaceutical composition according to the invention is more particularly useful for the treatment of the skin and of the mucosae and can be in the form of unguents, creams, milks, ointments, powders, impregnated tampons, syndets, solutions, gels, sprays, mousses, suspensions, stick lotions, shampoos, or washing bases. It can also be in the form of suspensions of microspheres or nanospheres or lipid or polymeric vesicles or polymeric patches and hydrogels permitting controlled release. This composition for topical administration can be in anhydrous form, in aqueous form or in the form of an emulsion.

The compounds are administered topically at a concentration generally ranging from 0.001 to 10 wt. %, preferably from 0.01 to 2 wt. %, relative to the total weight of the composition.

The compounds of formula (I) according to the invention, as well as their salts, pharmaceutically acceptable solvates and/or hydrates, also are useful in the cosmetics field, in particular in body and hair hygiene and more particularly for combating or preventing greasy skin, greasy hair or greasy scalp.

The present invention therefore features the cosmetic utilization of a composition comprising, in a physiologically acceptable carrier, at least one of the compounds of formula (I), optionally in the form of a salt, pharmaceutically acceptable solvate and/or hydrate, for body or hair hygiene.

The cosmetic compositions according to the invention containing, in a cosmetically acceptable carrier, at least one compound of formula (I) or one of its salts, pharmaceutically acceptable solvates and/or hydrates, can notably be in the form of a cream, a milk, a lotion, a gel, an unguent, an ointment, suspensions of microspheres or nanospheres or lipid or polymeric vesicles, impregnated tampons, solutions, sprays, mousses, sticks, soaps, shampoos or washing bases.

The concentration of compound of formula (I) in the cosmetic composition ranges from 0.001 to 3 wt. %, relative to the total weight of the composition.

The pharmaceutical and cosmetic compositions described above can in addition contain additives that are inert, or even pharmacodynamically active in the case of pharmaceutical compositions, or combinations of these additives, and notably:

wetting agents;

flavor-improving agents;

preservatives such as esters of parahydroxybenzoic acid;

stabilizers;

moisture regulators;

pH regulators;

agents for modifying osmotic pressure;

emulsifiers;

UV-A and UV-B filters;

antioxidants, such as α-tocopherol, butylated hydroxyanisole or butylated hydroxytoluene, superoxide dismutase, ubiquinol or certain chelators of metals;

depigmenting agents such as hydroquinone, azelaic acid, caffeic acid or kojic acid;

emollients;

moisturizers such as glycerol, PEG 400, thiamorpholinone, and derivatives thereof or urea;

carotenoids and, notably, β-carotene;

α-hydroxy acids and α-keto acids or their derivatives, such as lactic, malic, citric, glycolic, mandelic, tartaric, glyceric, and ascorbic acids, as well as their salts, amides or esters, or β-hydroxy acids or their derivatives, such as salicylic acid as well as their salts, amides or esters.

Of course, one skilled in the art will take care to select a compound or compounds to be added to these compositions in such a way that the advantageous properties associated intrinsically with the present invention are not, or substantially are not, altered by the addition envisaged.

Moreover, in a general way, the same preferences as those previously mentioned for the compounds of formula (I) apply mutatis mutandis to the medicaments, cosmetic and pharmaceutical compositions and applications employing the compounds of the invention.

In order to further illustrate the present invention and the advantages thereof, the following specific examples are given, including those of biological activity, it being understood that same are intended only as illustrative and in nowise limitative. In said examples to follow, all parts and percentages are given by weight, unless otherwise indicated.

The following abbreviations are used:
iPr=isopropyl, Ph=phenyl, p-tolyl=4-methylphenyl, p=para, m=meta, o=ortho, BiPh=biphenyl, Me=methyl,
o-biphenyl=o-BiPh=

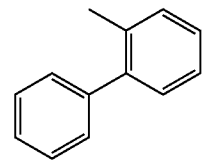

Example 1

1-(1-Benzenesulfonyl-cyclopentylmethyl)-3-(2,6-diisopropyl-phenyl)-urea, compound (I.1) where Y=—S(O)$_p$, p=2, n=0, R=H, R$_1$=R$_2$=iPr; R$_3$=H; R$_4$ and R'$_4$ are joined together to form a cyclopentyl; R$_5$=pH

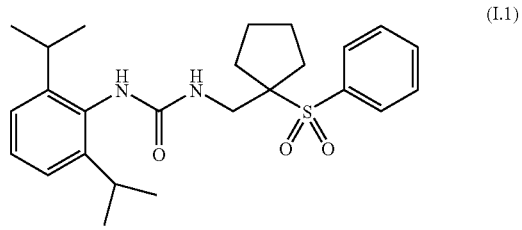

(I.1)

(a) Preparation of 1-Benzenesulfonyl-cyclopentanecarbonitrile 629 mg (2.8 mmol) of benzyltriethylammonium chloride is added to 5 g (27.6 mmol) of benzenesulfonylacetonitrile and 6.55 g (30.3 mmol) of 1,4-dibromobutane in 50 ml of a 50% aqueous soda solution. The reaction mixture is stirred at room temperature for 3 h. It is then diluted with water and extracted with ethyl acetate. The organic phases are combined and washed with water. They are dried over magnesium sulfate, filtered and the solvents are evaporated. The residue is purified on silica gel (heptane/ethyl acetate, 50/50, v/v). 6.35 g of 1-benzenesulfonyl-cyclopentanecarbonitrile is obtained in the form of a beige powder. (Yield=98%).

(b) Preparation of C-(1-Benzenesulfonyl-cyclopentyl)-methylamine 194 mg (5.1 mmol) of lithium aluminum hydride is added to a solution of 1 g (4.2 mmol) of 1-benzenesulfonyl-cyclopentanecarbonitrile in 20 ml of tetrahydrofuran. The reaction mixture is stirred at room temperature (RT) for 20 h. It is then hydrolyzed with 194 μl of water, 194 μl of a 15% soda solution and then 582 μl of water, stirred for 5 minutes, then filtered. The filtrate is evaporated and the residue is chromatographed on silica gel (dichloromethane then dichloromethane/methanol, 90/10, v/v). 420 mg of C-(1-benzenesulfonyl-cyclopentyl)-methylamine is obtained in the form of a colorless oil. (Yield=42%).

(c) Preparation of 1-(1-Benzenesulfonylcyclopentyl-methyl)-3-(2,6-diisopropyl-phenyl)-urea In a tube, under nitrogen, 157 mg (0.77 mmol) of 2-isocyanato-1,3-diisopropylbenzene is added to a solution of 168 mg (0.7 mmol) of C-(1-benzenesulfonyl-cyclopentyl)-methylamine in 3.5 ml of dichloromethane. The reaction mixture is stirred at RT for 3 h. The solvent is evaporated with a nitrogen stream. The paste obtained is taken up in heptane (5 mL) for crystallization. The white powder obtained is chromatographed on silica gel (dichloromethane then dichloromethane/methanol, 98/2, v/v). The oil obtained is crystallized from heptane. After filtration and drying, 135 mg of 1-(1-benzenesulfonylcyclopentylmethyl)-3-(2,6-diisopropyl-phenyl)-urea is obtained in the form of a white powder (m.p.=124° C., Yield=44%).

$^1$H NMR (CDCl$_3$, 400 MHz): 1.19-1.33 (m, 12H), 1.56 (m, 2H), 1.66 (m, 4H), 2.41 (m, 2H), 3.29 (m, 2H), 3.4 (d, J=4.8 Hz, 2H), 5.46 (br, ~1H), 6.06 (br, 1H), 7.23-7.26 (m, 2H), 7.37 (t, J=7.6 Hz, 1H), 7.46-7.50 (m, 2H), 7.6-7.66 (m, 3H).

Example 2

1-(2,6-Diisopropyl-phenyl)-3-[1-(toluene-4-sulfonyl)-cyclopentylmethyl]-urea, compound (I.2) where Y=—S(O)$_p$, p=2, n=0, R=H, R$_1$=R$_2$=iPr; R$_3$=H; R$_4$ and R'$_4$ are joined together to form a cyclopentyl; R$_5$=p-tolyl

(a) Preparation of (Toluene-4-sulfonyl)-acetonitrile 3.37 g (28 mmol) of bromoacetonitrile and 640 mg (2.8 mmol) of benzyltriethylammonium chloride are added to a solution of 5 g (28 mmol) of sodium 4-methyl-benzenesulfinate in 50 ml of toluene and 50 ml of dimethylformamide. The reaction mixture is stirred at room temperature for 24 h. The heterogeneous mixture is filtered. The filtrate is evaporated and then purified on silica gel (heptane then heptane/ethyl acetate, 60/40 v/v). The product is triturated in heptane then filtered and dried. 2.95 g of (toluene-4-sulfonyl)-acetonitrile is obtained in the form of a pale yellow powder. (Yield=54%).

(b) Preparation of 1-(Toluene-4-sulfonyl)-cyclopentanecarbonitrile

Similarly to Example 1 paragraph (a), by reaction of 2 g (10.2 mmol) of (toluene-4-sulfonyl)-acetonitrile with 1.35 ml (11.3 mmol) of 1,4-dibromobutane, 50 ml of aqueous soda solution, 233 mg (1 mmol) of benzyltriethylammonium chloride. 2.14 g of 1-(toluene-4-sulfonyl)cyclopentanecarbonitrile is obtained in the form of a brown powder. (Yield=84%)

(c) Preparation of C-[1-(Toluene-4-sulfonyl)-cyclopentyl]-methylamine

Similarly to Example 1(b), by reaction of 1.1 g (4.4 mmol) of 1-(toluene-4-sulfonyl)-cyclopentanecarbonitrile with 200 mg of aluminum lithium hydride. 400 mg of C-[1-(toluene-4-sulfonyl)-cyclopentyl]-methylamine is obtained in the form of an orange solid. (Yield=36%).

(d) Preparation of 1-(2,6-Diisopropyl-phenyl)-3-[1-(toluene-4-sulfonyl)-cyclopentylmethyl]-urea Similarly to Example 1(c), by reaction of 200 mg (0.8 mmol) of C-[1-(toluene-4-sulfonyl)-cyclopentyl]-methylamine with 177 mg (0.87 mmol) of 2-isocyanato-1,3-diisopropyl-benzene. 276 mg of 1-(2,6-diisopropyl-phenyl)-3-[1-(toluene-4-sulfonyl)cyclopentylmethyl]-urea is obtained in the form of an off-white powder. (Yield=77%).

$^1$H NMR (CDCl$_3$, 400 MHz): 1.19-1.32 (m, 12H), 1.53-1.67 (m, 6H), 2.11-2.18 (m, 2H), 2.42 (s, 3H), 3.29 (m, 2H), 3.40 (d, J=5.2 Hz, 2H), 5.51 (br, 1H), 5.78 (br, 1H), 7.23-7.28 (m, 4H), 7.37 (t, J=8.0 Hz, 1H), 7.52 (br, 2H).

Example 3

1-(2-Benzenesulfonyl-indan-2-ylmethyl)-3-(2,6-diisopropyl-phenyl)-urea, compound (I.3) where Y=—S(O)$_p$, p=2, n=0, R=H, R$_1$=R$_2$=iPr; R$_3$=H; R$_4$ and R'$_4$ are joined together to form an indanyl; R$_5$=Ph

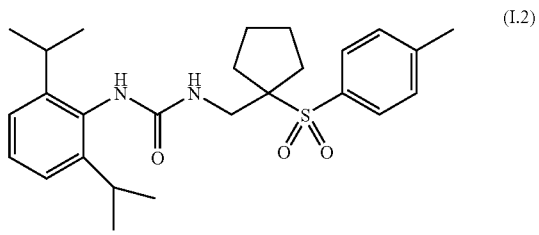

(I.2)

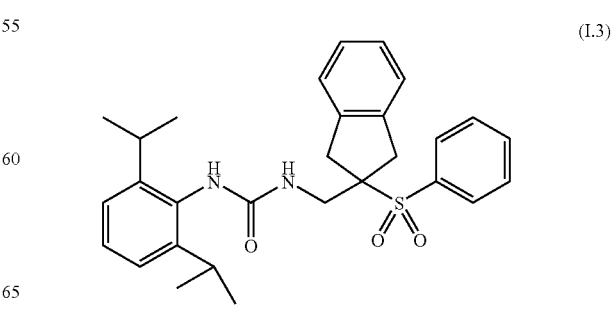

(I.3)

(a) Preparation of 2-Benzenesulfonyl-indane-2-carbonitrile

Similarly to Example 1(a), by reaction of 5 g (27.6 mmol) of benzenesulfonyl-acetonitrile with 8 g (30.4 mmol) of a,a'-dibromo-o-xylene, 50 ml of aqueous soda solution, 629 mg (2.8 mmol) of benzyltriethylammonium chloride. 2.1 g of 2-benzenesulfonyl-indane-2-carbonitrile is obtained in the form of a white solid. (Yield=27%).

(b) Preparation of C-(2-Benzenesulfonyl-indan-2-yl)-methylamine

Similarly to Example 1(b), by reaction of 1 g (3.5 mmol) of 2-benzenesulfonyl-indane-2-carbonitrile with 161 mg (4.2 mmol) of lithium aluminum hydride. 168 mg of C-(2-benzenesulfonyl-indan-2-yl)-methylamine is obtained in the form of a brown oil. (Yield=17%).

(c) Preparation of 1-(2-Benzenesulfonyl-indan-2-ylmethyl)-3-(2,6-diisopropyl-phenyl)-urea Similarly to Example 1(c), by reaction of 168 mg (0.6 mmol) of C-(2-benzenesulfonyl-indan-2-yl)-methylamine with 131 mg (0.64 mmol) of 2-isocyanato-1,3-diisopropyl-benzene. 106 mg of 1-(2-benzenesulfonyl-indan-2-ylmethyl)-3-(2,6-diisopropyl-phenyl)-urea is obtained in the form of a white solid. (Yield=36%).

$^1$H NMR (CDCl$_3$, 400 MHz): 1.2-1.38 (m, 12H), 2.96 (d, J=16.7 Hz, 2H), 3.31 (m, 2H), 3.55 (d, J=16.8 Hz, 2H), 3.64 (d, J=5.2 Hz, 2H), ~5.55 (br, 1H), 5.80 (br, 1H), 7.05 (m, 4H), 7.26 (s, 2H), 7.43 (m, 3H), 7.6 (m, 1H), 7.65 (br, 2H).

Example 4

1-(1-Benzylsulfanyl-cyclohexylmethyl)-3-(2,6-diisopropyl-phenyl)-urea, compound (I.4) where Y=S, p=0, n=1, R=H, R$_1$=R$_2$=iPr; R$_3$=H; R$_4$ and R'$_4$ are joined together to form a cyclohexyl; R$_5$=Ph

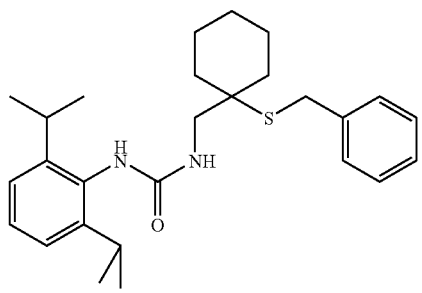

(I.4)

(a) Preparation of (1-Nitromethyl-cyclohexylsulfanylmethyl)-benzene 1.05 ml (10 mmol) of cyclohexanone, 5.5 ml (101 mmol) of nitromethane, 2.1 ml (21 mmol) of piperidine are added to a solution of 5 ml (42 mmol) of benzylmercaptan in 20 ml of acetonitrile. The solution is refluxed for 4 h. At room temperature, the mixture is evaporated and the residue is chromatographed on silica gel (heptane then heptane/ethyl acetate, 50/50, v/v). 600 mg of (1-nitromethyl-cyclohexylsulfanylmethyl)-benzene is obtained in the form of a colorless oil. (Yield=22%).

(b) Preparation of C-(1-Benzylsulfanyl-cyclohexyl)-methylamine

A solution of 500 mg (1.88 mmol) of (1-nitromethyl-cyclohexyl-sulfanylmethyl)-benzene in 20 ml of ethyl ether is added dropwise to 86 mg (2.26 mmol) of lithium aluminum hydride in 10 ml of ethyl ether at 0° C. It is stirred for 2 hours at 0° C. The reaction is stopped by adding 100 µl of water, 100 µl of 15% soda and then 500 µl of water. The mixture is then filtered on Celite and the filtrate is evaporated. The residue is purified on silica gel (heptane/ethyl acetate, 50/50, v/v then ethyl acetate then ethyl acetate/methanol, 50/50 v/v). 125 mg of C-(1-benzylsulfanyl-cyclohexyl)-methylamine is obtained in the form of a colorless oil. (Yield=28%).

(c) Preparation of 1-(1-Benzylsulfanyl-cyclohexylmethyl)-3-(2,6-diisopropyl-phenyl)-urea Similarly to Example 1(c), by reaction of 120 mg (0.51 mmol) of C-(1-benzylsulfanyl-cyclohexyl)-methylamine with 125 µl (0.61 mmol) of 2,6-diisopropylphenylisocyanate. 101 mg of 1-(1-benzylsulfanyl-cyclohexylmethyl)-3-(2,6-diisopropyl-phenyl)-urea is obtained in the form of a white solid. (m.p.=156° C., Yields 45%).

Mass: 439. HPLC: 96.6%.

$^1$H NMR (CDCl$_3$, 400 Mz): 1.18 (s, 6H); 1.23 (s, 6H); 1.41-1.65 (m, 10H); 3.24-3.24 (d, 2H); 3.26-3.36 (m, 2H); 3.43 (s, 2H); 4.75 (s, 1H); 5.70 (s, 1H); 7.01 (s, 2H); 7.17 (d, 3H); 7.25-7.28 (m, 2H); 7.38-7.42 (m, 1H).

Example 5

Biological Tests

The compounds of formula (I) according to the invention were tested to evaluate their inhibitory activity with respect to the enzyme ACAT-1 based on the following work: "Identification of ACAT1- and ACAT2-specific inhibitors using a novel, cell based fluorescence assay: individual ACAT uniqueness", J. lipid. Res (2004) vol 45, pages 378-386. The principle of this test is based on the use of NBD-cholesterol, an analogue of cholesterol with fluorescence depending on its environment. When it is in a polar environment it is weakly fluorescent, whereas in a non-polar environment it is strongly fluorescent. Free NBD-cholesterol localizes in the cell membranes and is weakly fluorescent in this polar environment. When NBD-cholesterol is esterified by ACAT, the ester of NBD-cholesterol localizes in the non-polar lipid droplets and is then strongly fluorescent.

The following method is used: HepG2 cells are incubated in the presence of NBD-cholesterol (1 µg/ml) and of the test compound of formula (I) in black, transparent-bottom 96-well plates at a rate of 30000 cells per well. After incubation for 6 h at 37° C., under 5% CO$_2$, the mixture is removed by inversion and the cells are washed with 2×100 µl of PBS. After adding 50 µl of lysis buffer (NaPO$_4$ 10 mM, Igepal 1%) the plates are agitated for 5 min and, read in fluorescence (excitation 490 nm, emission 540 nm) on a FUSION instrument (Perkin Elmer). As an illustration, an IC$_{50}$ of 71 nM is obtained for compound (I.4)

Example 6

Examples of Formulations

Various specific formulations based on the compounds according to the invention are given below.

A—Oral Administration:
(a) Tablet of 0.2 g:

| | |
|---|---|
| Compound (I.3) | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

(b) Oral Suspension in 5 ml Ampoules:

| | |
|---|---|
| Compound (I.1) | 0.001 g |
| Glycerol | 0.500 g |
| 70% sorbitol | 0.500 g |
| Sodium saccharinate | 0.010 g |
| Methyl parahydroxybenzoate | 0.040 g |
| Flavoring | qs |
| Purified water | q.s. 5 ml |

B—Topical Administration:
(a) Unguent:

| | |
|---|---|
| Compound (I.2) | 0.300 g |
| White petroleum jelly codex | q.s. 100 g |

(d) Lotion:

| | |
|---|---|
| Compound (I.4) | 0.100 g |
| Polyethylene glycol (PEG 400) | 69.900 g |
| 95% ethanol | 30.000 g |

(e) Hydrophobic Unguent:

| | |
|---|---|
| Compound (I.1) | 0.300 g |
| Isopropyl myristate | 36.400 g |
| Silicone oil ("Rhodorsil 47 V 300") | 36.400 g |
| Beeswax | 13.600 g |
| Silicone oil ("Abil 300,000 cSt") | q.s. 100 g |

(f) Non-Ionic Oil-in-Water Cream:

| | |
|---|---|
| Compound (I.2) | 1.000 g |
| Cetyl alcohol | 4.000 g |
| Glycerol monostearate | 2.500 g |
| Stearate of PEG 50 | 2.500 g |
| Shea butter | 9.200 g |
| Propylene glycol | 2.000 g |
| Methyl parahydroxybenzoate | 0.075 g |
| Propyl parahydroxybenzoate | 0.075 g |
| Sterile demineralized water | q.s. 100 g |

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A phenylurea compound having the following formula (I):

$$\text{(I)}$$

in which:
Y is O or $S(O)_p$,
p is equal to 0 or 2,
n is equal to 0, 1 or 2
R is a hydrogen atom, a $(C_1-C_6)$alkyl radical, a —$CH_2$—$NR_6R_7$ radical, a —C(O)—$NR_6R_7$ radical or a —C(S)—$NR_6R_7$ radical, wherein $R_6$ is a hydrogen atom or a $(C_1-C_4)$alkyl radical and $R_7$ is a hydrogen atom, a phenyl or a cycloalkyl radical,
$R_1$ is a hydrogen atom, a $(C_1-C_6)$alkyl radical or an atom of chlorine, bromine or fluorine,
$R_2$ is a $(C_1-C_6)$alkyl radical,
$R_3$ is a hydrogen atom or a $(C_1-C_6)$alkyl radical,
$R_4$ and $R'_4$ are identical and are each a $(C_1-C_6)$alkyl radical or alternatively $R_4$ and $R'_4$ are joined together and form, with the carbon atom from which they depend, a cycloalkyl group, an indanyl group, or a saturated heterocyclic group selected from the groups piperidine, tetrahydropyran, pyrrolidine, tetrahydrothiophene, tetrahydrofuran and azetidine, wherein the groups piperidine, pyrrolidine and azetidine are optionally substituted on the nitrogen atom with an $R_8$, —$C(O)R_8$ or —$SO_2R_8$ radical, wherein $R_8$ is a $(C_1-C_4)$alkyl radical,
$R_5$ is an unsubstituted phenyl radical or a phenyl radical substituted with one to three substituents, which may be identical or different, selected from the atoms of chlorine, bromine or fluorine, the radicals $(C_1-C_6)$alkyl, cycloalkyl, trifluoromethyl, hydroxy, phenyl, 2-pyridyl, 3-pyridyl, 4-pyridyl, $(C_1-C_6)$alkoxy, phenoxy, $(C_1-C_6)$alkylthio, trifluoromethoxy, or —$NR_9R_{10}$, wherein $R_9$ and $R_{10}$, which may be identical or different, represent, each independently, a hydrogen atom or a $(C_1-C_4)$alkyl radical, or a pharmaceutically acceptable salt, solvate or hydrate thereof.

2. A phenylurea compound as defined by claim 1, wherein formula (I):
Y is O, $S(O)_p$,
p is equal to 0 or 2,
n is equal to 0, 1 or 2, R is a hydrogen atom, R₁ is a methyl, ethyl, isopropyl or tert-butyl radical, R₂ is a methyl, ethyl, isopropyl or tert-butyl radical, R₃ is a hydrogen atom, R₄ and R'₄ are identical and are each an ethyl radical or alternatively R₄ and R'₄ are joined together and form, with the carbon atom from which they depend, either a cyclopentyl, cyclohexyl, cycloheptyl, or indanyl group, or a tetrahydropyran group, piperidine group, or piperidine group substituted on the nitrogen atom with an R₈, —C(O)R₈ or —SO₂R₈ radical, wherein R₈ is a (C₁-C₄) alkyl radical, R₅ is an o-, m- or p-biphenyl, o-, m- or p-iodophenyl, o-, m- or p-(2-pyridyl)phenyl, o-, m- or p-(3-pyridyl)phenyl or an o-, m- or p-(4-pyridyl)phenyl radical, an unsubstituted phenyl radical, a phenyl radical substituted with one to three substituents, identical or different, selected from methyl, ethyl, trifluoromethyl, fluorine, chlorine, hydroxy.

3. A phenylurea compound as defined by claim 1, wherein formula (I), n is equal to 0 or 1.

4. A phenylurea compound as defined by claim 1, wherein formula (I), R is a hydrogen atom.

5. A phenylurea compound as defined by claim 1, wherein formula (I), R₁ is an isopropyl radical.

6. A phenylurea compound as defined by claim 1, wherein formula (I), R₂ is an isopropyl radical.

7. A phenylurea compound as defined by claim 1, wherein formula (I), R₃ is a hydrogen atom.

8. A phenylurea compound as defined by claim 1, wherein formula (I), R₄ and R'₄ are joined together and form, with the carbon atom from which they depend, a cyclopentyl, cyclohexyl or indanyl group.

9. A phenylurea compound as defined by claim 1, wherein formula (I), R₅ is an unsubstituted phenyl radical, or a phenyl radical substituted with a methyl radical or with a phenyl radical.

10. A phenylurea compound as defined by claim 1, selected from the group consisting of the following compounds, and the pharmaceutically acceptable salts, solvates and hydrates thereof:

1-(1-Benzenesulfonyl-cyclopentylmethyl)-3-(2,6-diisopropyl-phenyl)-urea, 1-(2,6-Diisopropyl-phenyl)-3-[1-(toluene-4-sulfonyl)-cyclopentylmethyl]urea, 1-(2-Benzenesulfonyl-indan-2-ylmethyl)-3-(2,6-diisopropyl-phenyl)-urea, 1-(1-Benzylsulfanyl-cyclohexylmethyl)-3-(2,6-diisopropyl-phenyl)-urea, 1-(1-Benzyloxy-cyclohexylmethyl)-3-(2,6-diisopropyl-phenyl)-urea, 1-(2,6-Diisopropyl-phenyl)-3-(1-phenoxy-cyclohexylmethyl)-urea, 1-(2,6-Diisopropyl-phenyl)-3-(1-phenylsulfanyl-cyclohexylmethyl)-urea, 1-(2,6-Diisopropyl-phenyl)-3-(1-p-tolylsulfanyl-cyclohexylmethyl)-urea, 1-[1-(Biphenyl-2-ylsulfanyl)-cyclohexylmethyl]-3-(2,6-diisopropyl-phenyl)-urea, 1-[1-(Biphenyl-2-ylsulfanyl)-cyclopentylmethyl]-3-(2,6-diisopropyl-phenyl)-urea, and 1-[1-(Biphenyl-2-yloxy)-cyclohexylmethyl]-3-(2,6-diisopropyl-phenyl)-urea.

11. A medicament comprising at least one phenylurea compound as defined by claim 1, or salt, solvate or hydrate thereof.

12. A pharmaceutical composition as defined by claim 11, comprising a concentration of compound(s) of formula (I) ranging from 0.001 to 10% by weight relative to the total weight thereof.

13. A pharmaceutical composition comprising, formulated into a physiologically acceptable carrier, at least one phenylurea compound as defined by claim 1, or salt, solvent or hydrate thereof.

14. A pharmaceutical composition as defined by claim 13, comprising a concentration of compound(s) of formula (I) ranging from 0.01 to 2% by weight relative to the total weight thereof.

15. A pharmaceutical composition as defined by claim 13, formulated for topical application.

16. A pharmaceutical composition as defined by claim 15, comprising a cream, a milk, a lotion, a gel, an ointment, a pomade, suspensions of microspheres or nanospheres or lipid or polymeric vesicles, impregnated swabs, solutions, sprays, foams, sticks, soaps, shampoos or washing bases.

17. A cosmetic composition comprising, formulated into a physiologically acceptable carrier, at least one phenylurea compound as defined by claim 1, or salt, solvent or hydrate thereof.

18. A cosmetic composition as defined by claim 17, comprising a concentration of compound(s) of formula (I) ranging from 0.001 to 3% by weight relative to the total weight thereof.

19. A cosmetic composition as defined by claim 17, formulated for body or hair hygiene.

20. A process for the preparation of a compound of formula (I) as defined by claim 1, which comprises the following stages: reacting a primary or secondary amine of formula (1):

$$HN\overset{R_3}{\underset{R_4\ R'_4}{\diagdown}}\overset{Y}{\diagup}\overset{(CH_2)_n}{\underset{R'_5}{\diagdown}} \quad (1)$$

wherein:
R'₅ is the group R₅ or a precursor of the group R₅ with a compound of formula (2):

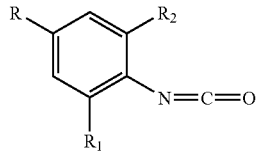

(2)

to obtain a compound of formula (I'):

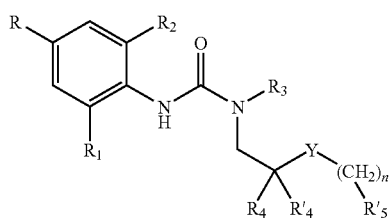

(I')

wherein R'₅ is the group R₅ or a precursor of the group R₅, and then, when R'₅ is different from R₅, transforming the group R'₅ to obtain the desired group R₅.

21. A method for treating disorders of the sebaceous gland, hyperseborrhoea, acne, seborrhoeic dermatitis, atopic dermatitis, rosacea, ocular rosacea, blepharitis, meibomitis, chalazion, dry eye, conjunctivitis or keratoconjunctivitis, comprising administering to an individual in need of such treatment, for such period of time as required to elicit the desired result, a thus effective amount of at least one phenylurea compound as defined by claim 1, or salt, solvent or hydrate thereof.

22. The method as defined by claim 21, wherein the disorder is acne.

* * * * *